United States Patent
Osafune et al.

(10) Patent No.: US 9,121,011 B2
(45) Date of Patent: Sep. 1, 2015

(54) METHOD FOR INDUCING DIFFERENTIATION OF HUMAN PLURIPOTENT STEM CELL INTO INTERMEDIATE MESODERM CELL

(75) Inventors: Kenji Osafune, Kyoto (JP); Shin-ichi Mae, Kyoto (JP); Masatoshi Kajiwara, Kyoto (JP)

(73) Assignee: KYOTO UNIVERSITY, Kyoto-shi (JP)

(*) Notice: Subject to any disclaimer, the term of this patent is extended or adjusted under 35 U.S.C. 154(b) by 0 days.

(21) Appl. No.: 13/811,163

(22) PCT Filed: Jul. 21, 2011

(86) PCT No.: PCT/JP2011/067181
§ 371 (c)(1),
(2), (4) Date: Jan. 18, 2013

(87) PCT Pub. No.: WO2012/011610
PCT Pub. Date: Jan. 26, 2012

(65) Prior Publication Data
US 2013/0122536 A1 May 16, 2013

Related U.S. Application Data

(60) Provisional application No. 61/366,379, filed on Jul. 21, 2010, provisional application No. 61/451,825, filed on Mar. 11, 2011.

(51) Int. Cl.
| | |
|---|---|
| *C12N 5/071* | (2010.01) |
| *C12N 5/074* | (2010.01) |
| *C12N 5/073* | (2010.01) |
| *C12N 5/0735* | (2010.01) |
| *G01N 33/50* | (2006.01) |

(52) U.S. Cl.
CPC ............ *C12N 5/0696* (2013.01); *C12N 5/0603* (2013.01); *C12N 5/0606* (2013.01); *G01N 33/5073* (2013.01); *C12N 2501/155* (2013.01); *C12N 2501/16* (2013.01); *C12N 2501/415* (2013.01); *C12N 2506/45* (2013.01)

(58) Field of Classification Search
CPC . C12N 5/0696; C12N 2506/45; C12N 5/0606
See application file for complete search history.

(56) References Cited

U.S. PATENT DOCUMENTS

2010/0166713 A1* 7/2010 Dalton et al. ............... 424/93.7

OTHER PUBLICATIONS

Wang et al. (Developmental Biology. 2005; 288: 582-594).*
Nostro et al (Cell Stem Cell. Jan. 2008; 2: 60-71).*
Xu et al. (Nature Biotechnology. 2001; 19: 971-974).*
Ying et al. (Nature. 2008; 453: 519-524).*
Sato et al (Nature Medicine. 2004; 10(1): 55-63).*
Batchelder et al. (Differentiation. 2009; 78(1): 45-56).*
Nishikawa et al. (Nature Reviews: Molecule Cell Biology. 2008; 9: 725-729).*
Mugford et al. (Developmental Biology. 2008; 324: 88-89).*
Batchelder et al., "Renal ontogeny in the rhesus monkey (*Macaca mulatta*) and directed differentiation of human embryonic stem cells towards kidney precursors", Differentiation, Jul. 2009, vol. 78(1), pp. 45-56.
International Search Report mailed on Sep. 13, 2011, issued in PCT/JP2011/067181.
Kim et al., "Nephrogenic factors promote differentiation of mouse embryonic stem cells into renal epithelia", J. Am. Soc. Nephrol., Dec. 2005, vol. 16(12), pp. 3527-3534.
Mae et al., "Combination of small molecules enhances differentiation of mouse embryonic stem cells into intermediate mesoderm through BMP7-positive cells", Mar. 19, 2010, Biochem. Biophys. Res. Commun., vol. 393(4), pp. 877-882.
Mugford et al., "OsrI expression demarcates a multi-potent population of intermediate mesoderm that undergoes progressive restriction to an OsrI-dependent nephron progenitor compartment within the mammalian kidney", Dev. Biol., Dec. 1, 2008, vol. 324(1), pp. 88-98.
Ren et al., "Differentiation of murine embryonic stem cells toward renal lineages by conditioned medium from ureteric bud cells in vitro", Acta Biochim. Biophys. Sin, (Shanghai), Jul. 2010, vol. 42(7), pp. 464-471.
Vigneau et al., "Mouse Embryonic Stem Cell-Derived Embryoid Bodies Generate Progenitors That Integrate Long Term into Renal Proximal Tubules In Vivo", J. Am. Soc. Nephrol. Jun. 2007, vol. 18(6), pp. 1709-1720.
Written Opinion of The International Searching Authority mailed on Sep. 13, 2011, issued in PCT/JP2011/067181.

* cited by examiner

*Primary Examiner* — Scott Long
(74) *Attorney, Agent, or Firm* — Birch, Stewart, Kolasch & Birch, LLP (57) ABSTRACT

The present invention relates to: a method for producing an intermediate mesoderm cell from a human pluripotent stem cell, comprising a step of culturing the human pluripotent stem cell in a medium containing Activin A and Wnt or a functional equivalent of Wnt and a step of culturing cells in a medium containing BMP and Wnt or a functional equivalent of Wnt; to a method for producing a metanephric cell from the intermediate mesoderm cell produced by the first method; to a human pluripotent stem cell having a foreign reporter gene in the chromosome wherein the gene is expressed interlocked with the expression of endogenous OSR1; to a method for screening for an inducer for differentiation into intermediate mesoderm using the human pluripotent stem cell; and to a kit for inducing the differentiation into an intermediate mesoderm cell.

16 Claims, 3 Drawing Sheets
(1 of 3 Drawing Sheet(s) Filed in Color)

Bar = 100mm.

c

METHOD FOR INDUCING DIFFERENTIATION OF HUMAN PLURIPOTENT STEM CELL INTO INTERMEDIATE MESODERM CELL

CROSS REFERENCE TO RELATED APPLICATIONS

This application is the National Phase of PCT/JP2011/067181 filed on Jul. 21, 2011, which claims priority under 35 U.S.C. 119(e) to U.S. Provisional Application Nos. 61/366,379 and 61/451,825 filed on Jul. 21, 2010 and Mar. 11, 2011 respectively, all of which are hereby expressly incorporated by reference into the present application.

TECHNICAL FIELD

The present invention relates to a method for inducing differentiation of a pluripotent stem cell into an intermediate mesoderm cell.

The present invention also relates to a human pluripotent stem cell having a reporter gene in the chromosome, whose expression is interlocked with the expression of endogenous OSR1, and to a method for screening for a differentiation inducer using the cell.

BACKGROUND ART

The kidney is an important organ that functions to keep physical health, by which waste products, such as harmful or detrimental substances generated as a result of metabolic activity within a living organism, are removed from the blood by filtration.

An example of kidney disorders is kidney failure, and a therapeutic method therefor is artificial dialysis, for example. However, the burden imposed by medical expenses required for the therapeutic method is high, and thus the kidney failure is still a world-wide problem, not only from medical aspect, but also from medical economic aspect. Another example of a therapeutic method for kidney failure is renal transplantation, but in Japan especially, shortage of donor organs is severe.

Meanwhile, pluripotent cells such as embryonic stem cells (ES cells) and induced pluripotent stem cells (iPS cells), which can be obtained via introduction of an undifferentiated cell-specific gene(s) into somatic cells, have been reported (U.S. Pat. No. 5,843,780 or WO 2007/069666). Therefore, as a therapeutic method for kidney failure, a therapeutic method that involves transplanting renal cells obtained by inducing differentiation of these pluripotent stem cells has been investigated. Moreover, developing therapeutic agents using homogeneous renal cells from these pluripotent stem cells is also under consideration.

The mammalian kidney is formed through three stages consisting of pronephros, mesonephros, and metanephros. Among these stages, the metanephros is known to be generated in the posterior region of the intermediate mesoderm.

In this context, although a method for inducing differentiation of mouse pluripotent stem cells into intermediate mesoderm for nephrogenesis has been investigated (Mae S, et al. (2010), Biochem Biophys Res Commun. 393: 877-882), to date, the efficient induction of the differentiation of human pluripotent stem cells into intermediate mesoderm has never been reported.

SUMMARY OF THE INVENTION

Problem to be Solved by the Invention

An object of the present invention is to provide a human pluripotent stem cell having a reporter gene in the chromosome, whose expression is interlocked with the expression of endogenous OSR1, and further a method for inducing the differentiation of a human pluripotent stem cell into an intermediate mesoderm cell, comprising a step of culturing with a medium containing Activin A and Wnt and a step of culturing with a medium containing BMP and Wnt.

Means for Solving the Problem

The present invention has the following characteristics.
[1] A method for producing an intermediate mesoderm cell from a human pluripotent stem cell, comprising the following steps (i) and (ii) of:
(i) culturing the human pluripotent stem cell in a medium containing Activin A and Wnt or a functional equivalent of Wnt, and then
(ii) culturing the cell obtained in the step (i) in a medium containing BMP and Wnt or a functional equivalent of Wnt.
[2] The method of [1] above, wherein the intermediate mesoderm cell is an OSR1-positive cell.
[3] The method of [1] or [2] above, wherein in the culture of the step (i), the human pluripotent stem cell is cultured in suspension to form a cell population or cell mass of the human pluripotent stem cell, and in the culture of the step (ii), the cell population or the cell mass is subjected to adhesion culture, thereby forming the intermediate mesoderm cell.
[4] The method of [1] or [2] above, further comprising, in the culture of the step (i), substantially separating the cell population or cell mass of human pluripotent stem cell into respective cells.
[5] The method of [4] above, wherein the step (i) further comprises adhering the separated cells to a Matrigel™-coated dish or a collagen-coated dish and then culturing the cells.
[6] The method of any one of [1] to [5] above, wherein in the step (i), the medium further contains fetal bovine serum (FBS).
[7] The method of any one of [1] to [5] above, wherein in the step (ii), the medium further contains a knockout serum replacement (KSR).
[8] The method of any one of [1] to [7] above, wherein the Wnt is Wnt3a.
[9] The method of any one of [1] to [7] above, wherein the functional equivalent of Wnt is a GSK3β inhibitor.
[10] The method of [9] above, wherein the GSK3β inhibitor is CHIR99021.
[11] The method of any one of [1] to [10] above, wherein the BMP is BMP7.
[12] The method of [3] above, wherein the culture in the step (i) is performed for a culture period ranging from 2 to 5 days, preferably 2 days, and the culture in the step (ii) is performed for a culture period ranging from 14 to 18 days, preferably 16 days.
[13] The method of [4] above, wherein the culture in the step (i) is performed for a culture period ranging from 2 to 5 days, preferably 2 days, and the culture in the step (ii) is performed for a culture period ranging from 7 to 10 days, preferably 8 days.

[14] The method of any one of [1] to [13] above, wherein the human pluripotent stem cell is a human iPS cell or a human ES cell.

[15] The method of any one of [1] to [14] above, wherein the human pluripotent stem cell has a foreign reporter gene in the chromosome, wherein expression of the gene is interlocked with the expression of endogenous OSR1.

[16] The method of [15] above, wherein the reporter gene is a DNA encoding a fluorescent protein, a luminescent protein, GUS, or LacZ.

[17] The method of [15] or [16] above, wherein the pluripotent stem cell is a human iPS cell.

[18] A method for producing a metanephric cell, comprising inducing intermediate mesoderm from a human pluripotent stem cell by the method of any one of [1] to [17] above comprising the steps (i) and (ii) and further continuously performing the step (ii) to produce the metanephric cell.

[19] A human pluripotent stem cell having a foreign reporter gene in the chromosome, wherein the gene is expressed interlocked with the expression of endogenous OSR1.

[20] The human pluripotent stem cell of [19] above, wherein the reporter gene is a DNA encoding a fluorescent protein, a luminescent protein, GUS, or LacZ.

[21] The human pluripotent stem cell of [19] or [20] above, wherein the pluripotent stem cell is a human iPS cell.

[22] A method for screening for an inducer for differentiation into intermediate mesoderm, wherein the method comprises culturing the human pluripotent stem cell of any one of [19] to [21] above in the presence of a candidate substance and examining whether the candidate substance has an ability to induce the differentiation into intermediate mesoderm.

[23] A kit for inducing the differentiation into an intermediate mesoderm cell, comprising Activin A, Wnt or a functional equivalent thereof, and BMP, in different containers.

[24] The kit of [23], wherein the Activin A and the Wnt or a functional equivalent thereof is contained in a culture medium.

[25] The kit of [23], wherein the BMP and the Wnt or a functional equivalent thereof is contained in a culture medium.

[26] The kit of any one of [23] to [25], further comprising a human pluripotent stem cell.

[27] The kit of [26], wherein the human pluripotent stem cell is a cell as defined in any one of [19] to [21].

Human pluripotent stem cells having a reporter gene in the chromosome, whose expression is interlocked with the expression of endogenous OSR1, and artificial human intermediate mesoderm cells derived from the human pluripotent stem cells, can be prepared by the above-mentioned methods of the present invention.

BRIEF DESCRIPTION OF DRAWINGS

The patent or application file contains at least one color drawing. Copies of this patent or patent application publication with color drawing will be provided by the USPTO upon request and payment of the necessary fee.

In FIG. 3a, the vertical axis indicates PE intensity and the horizontal axis indicates GFP intensity.

MODES FOR CARRYING OUT THE INVENTION

Hereinafter, the present invention will be described in detail.

The present invention relates to a human pluripotent stem cell having a reporter gene in the chromosome, whose expression is interlocked with the expression of endogenous OSR1, and further to a method for inducing differentiation of a human pluripotent stem cell into an intermediate mesoderm cell using media supplemented with growth factors.

<Pluripotent Stem Cells>

Pluripotent stem cells that can be used in the present invention are stem cells having both pluripotency, by which the cells are capable of differentiating into all cells existing in the living body, and, proliferation potency. Examples of these pluripotent stem cells include, but are not limited to, embryonic stem (ES) cells, embryonic stem (ntES) cells from clone embryos obtained by nuclear transplantation, germline stem cells ("GS cells"), embryonic germ cells ("EG cells"), and induced pluripotent stem (iPS) cells. Examples of preferable pluripotent stem cells include ES cells, ntES cells, and iPS cells.

(A) Embryonic Stem Cell

ES cells are stem cells having pluripotency and an ability to proliferate by self-replication, which cells are established from the inner cell mass of early embryos (e.g., blastocysts) of a mammal such as human or mouse.

The ES cell is a stem cell derived from the inner cell mass of the blastocyst that is an embryo at 8-cell stage or morula stage of a fertilized egg. The ES cell has so-called pluripotency, which is an ability to differentiate into all cells for forming a matured body, and an ability to proliferate by self-replication. The ES cell was first discovered in mouse in 1981 (M. J. Evans and M. H. Kaufman (1981), Nature 292: 154-156), Thereafter, ES cell lines were established in primates including humans, monkeys, and the like (J. A. Thomson et al. (1998), Science 282:1145-1147; J. A. Thomson et al. (1995), Proc. Natl. Acad. Sci. USA, 92: 7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of an fertilized egg of a subject animal and then culturing the inner cell mass on a fibroblast feeder. Also, the maintenance of ES cells by subculture can be carried out by using a medium supplemented with substances such as leukemia inhibitory factor (LIF) and basic fibroblast growth factor (bFGF). Methods for establishing and maintaining human and monkey ES cells are described in H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222: 273-279; and H. Kawasaki et al. (2002), Proc. Natl. Acad. Sci. USA, 99: 1580-1585, for example.

As a medium for preparation of ES cells, a DMEM/F-12 medium supplemented with 0.1 mM 2-mercaptoethanol, 0.1 mM nonessential amino acids, 2 mM L-glutamate, 20% KSR (knockout serum replacement), and 4 ng/ml bFGF can be used, for example. Human ES cells can be maintained under wet atmosphere of 5% $CO_2$ at 37° C. Also, it is necessary for ES cells to subculture every 3 to 4 days. At this time, the subculture can be carried out by using 0.25% trypsin and 0.1 mg/ml collagenase IV in PBS (phosphate buffered saline) containing 1 mM $CaCl_2$ and 20% KSR, for example.

ES cells can be generally selected using the expression of gene markers such as alkaline phosphatase, Oct-3/4, Nanog, and the like, as indicators. In particular, human ES cells can be selected by detecting the expression of gene markers such as OCT-3/4 and NANOG by Real-Time PCR, and/or by detecting the cell surface antigens, i.e., SSEA-3, SSEA-4, TRA-1-60, and TRA-1-81, by immunostaining (Klimanskaya I, et al. (2006), Nature. 444: 481-485).

Human ES cell lines, such as KhES-1, KhES-2, and KhES-3, are available from the Institute for Frontier Medical Sciences, Kyoto University (Kyoto, Japan).

(B) Germline Stem Cell

The germline stem cell is a testis-derived pluripotent stem cell, serving as an origin for spermatogenesis. The germline stem cell can also be induced so as to differentiate into a variety of cell lines in a manner similar to that in ES cell. For example, the germline stem cell has properties such that a chimeric mouse can be produced when transplanted into the mouse blastocyst (M. Kanatsu-Shinohara et al. (2003) Biol. Reprod., 69:612-616; K. Shinohara et al. (2004), Cell, 119: 1001-1012). The germline stem cell is self-replicable in a medium containing a glial cell line-derived neurotrophic factor (GDNF), and the germline stem cell can be obtained by repeated subculture of the cell under culture conditions similar to those for ES cells (Masanori Takebayashi et al., (2008), Experimental Medicine, Vol. 26, No. 5 (Extra Number), pp. 41-46, YODOSHA (Tokyo; Japan)).

(C) Embryonic Germ Cell

The embryonic germ cell is a cell established from primordial germ cells at the prenatal period and has pluripotency similar to that of ES cells. Embryonic germ cells can be established by culturing primordial germ cells in the presence of a substance(s) such as LIF, bFGF, or stem cell factor (Y. Matsui et al. (1992), Cell, 70: 841-847; J. L. Resnick et al. (1992), Nature, 359:550-551).

(D) Induced Pluripotent Stem Cell

Induced (artificial) pluripotent stem (iPS) cells can be prepared by introducing a specific nuclear reprogramming substance(s) in the form of a nucleic acid (e.g., DNA, gene, RNA, etc) or protein into somatic cells, or by increasing the expression levels of the endogenous mRNA and proteins of the nuclear reprogramming substances, with the use of a certain agent(s). The iPS cells are somatic cell-derived artificial stem cells having properties almost equivalent to those of ES cells, such as pluripotency and an ability to proliferating by self-replication (K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; International Publication WO 2007/069666; and International Publication WO2010/068955). The nuclear reprogramming substance(s) may be a gene(s) specifically expressed in ES cells, a gene(s) playing an important role in maintenance of undifferentiation of ES cells, or a gene product(s) thereof such as protein(s) or mRNA(s). Examples of the nuclear reprogramming substances include, but are not limited to, Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb Esrrg, and Glis1. These reprogramming substances may be used in combination upon establishment of iPS cells. Such combination may contain at least one, two, or three reprogramming substances above and preferably contains three or four reprogramming substances above.

The nucleotide sequence information of the mouse or human cDNA of each of the above nuclear reprogramming substances and the amino acid sequence information of a protein encoded by the cDNA can be obtained by accessing to GenBank (NCBI, USA) or EMBL (Germany) accession numbers as described in WO 2007/069666. Also, the mouse and human cDNA and amino acid sequences information of L-Myc, Lin28, Lin28b, Esrrb, Esrrg, and Glis1 can be each obtained by accessing to the NCBI accession numbers shown in Table 1. Persons skilled in the art can prepare desired nuclear reprogramming substances by conventional techniques based on the cDNA or amino acid sequences information.

TABLE 1

| Gene name | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be introduced in the form of protein into somatic cells by a technique such as lipofection, binding with a cell membrane-permeable peptide, or microinjection. Alternatively, they can also be introduced in the form of DNA into somatic cells by a technique such as use of a vector such as virus, plasmid, or artificial chromosome, lipofection, use of liposomes, or microinjection. Examples of viral vectors include a retrovirus vector, a lentivirus vector (these are according to Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a Sendai virus vector (Proc Jpn Acad Ser B Phys Biol Sci. 85, 348-62, 2009). Also, examples of artificial chromosome vectors include a human artificial chromosome (HAC), a yeast artificial chromosome (YAC), and a bacterial artificial chromosome (BAC and PAC). As the plasmid, plasmids for mammalian cells can be used (Science, 322: 949-953, 2008). The above-described vectors can contain regulatory sequences such as a promoter, an enhancer, a ribosome binding sequence, a terminator, and a polyadenylation site or signal, so that a nuclear reprogramming substance can be expressed. Examples of the promoter usable herein include an EF1a promoter, a CAG promoter, an SRa promoter, an SV40 promoter, an LTR promoter, a CMV (cytomegalovirus) promoter, an RSV (Rous sarcoma virus) promoter, MoMuLV (Moloney murine leukemia virus) LTR, and an HSV-TK (herpes simplex virus thymidine kinase) promoter. Particularly preferable examples of such promoters include an EF1a promoter, a CAG promoter, MoMuLV LTR, a CMV promoter, and an SRα promoter. The above-described vectors may further contain, if necessary, a selection marker sequence such as a drug resistance gene (e.g., a kanamycin resistance gene, an ampicillin resistance gene, or a puromycin resistance gene), a thymidine kinase gene, and a diphtheria toxin gene or fragment thereof, and a reporter gene sequence such as a green fluorescent protein (GFP), β glucuronidase (GUS), or FLAG Also, in order to cleave both a gene encoding a nuclear reprogramming substance or a promoter and a promoter-binding gene which encodes a nuclear reprogramming substance, after introduction into somatic cells, the vector may have LoxP sequences located before and after the relevant portion. In another preferable embodiment, a method that involves incorporating a transgene into the chromosome using a transposon, causing transferase to act on cells using a plasmid vector or an adenovirus vector, and then completely removing the transgene from the chromosome can be used. An example of a preferable transposon is piggyBac that is a lepidopteran insect-derived transposon (Kaji, K. et al., Nature, 458: 771-775 (2009), Woltjen et al., *Nature,* 458: 766-770 (2009), WO 2010/012077). Furthermore, the vectors may also comprise sequences of replication origins for lymphotrophic herpes virus, BK virus, and Bovine papilloma virus and sequences involved in the replication, so that the sequences can be replicated without incorporation into the chromosome so as to be present episomally. For example, EBNA-1 and oriP sequences, or Large T and SV40ori sequences may be comprised in the vectors (WO 2009/115295, WO 2009/157201, and WO 2009/149233). Also, for simultaneously introducing two or more nuclear reprogramming substances, an expression vector that enables polycistronic expression may be used. For polycistronic expression, the sequences of IRES or a foot and mouth disease virus (FMDV) 2A coding region may be linked between the gene-coding sequences (Science, 322: 949-953, 2008, WO 2009/092042, and WO 2009/152529).

Upon nuclear reprogramming, to improve the efficiency for inducing iPS cells, in addition to the above-described reprogramming substances or factors, histone deacetylase (HDAC) inhibitors [e.g., low-molecular-weight inhibitors such as valproic acid (VPA) (Nat. Biotechnol., 26(7): 795-797 (2008)), trichostatin A, sodium butyrate, MC 1293, and M344, and nucleic acid expression inhibitors such as siRNA and shRNA against HDAC (e.g., HDAC1 siRNA Smartpool™ (Millipore) and HuSH 29 mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [e.g., low-molecular-weight inhibitors such as BIX-01294 (Cell Stem Cell, 2: 525-528 (2008)) and nucleic acid expression inhibitors such as siRNA and shRNA against G9a (e.g., G9a siRNA (human) (Santa Cruz Biotechnology))], L-channel calcium agonists (e.g., Bayk8644) (Cell Stem Cell, 3, 568-574 (2008)), p53 inhibitors (e.g., siRNA and shRNA against p53) (Cell Stem Cell, 3, 475-479 (2008)), Wnt Signaling Activator (e.g., soluble Wnt3a) (Cell Stem Cell, 3, 132-135 (2008)), growth factors such as LIF or bFGF, ALK5 inhibitors (e.g., SB431542) (Nat. Methods, 6: 805-8 (2009)), mitogen-activated protein kinase signalling inhibitors, glycogen synthase kinase-3 inhibitors (PloS Biology, 6(10), 2237-2247 (2008)), miRNA such as miR-291-3p, miR-294, and miR-295 (R. L. Judson et al., Nat. Biotech., 27: 459-461 (2009)), for example, can be used.

Examples of agents used in the method for increasing the expression level of the endogenous protein of a nuclear reprogramming substance with the use of such agents include 6-bromoindirubin-3'-oxime, indirubin-5-nitro-3'-oxime, valproic acid, 2-(3-(6-methylpyridin-2-yl)-1H-pyrazol-4-yl)-1, 5-naphthyridine, 1-(4-methylphenyl)-2-(4,5,6,7-tetrahydro-2-imino-3 (2H)-benzothiazolyl)ethanone HBr(pifithrin-alpha), prostaglandin J2, and prostaglandin E2 (WO 2010/068955).

Examples of a culture medium for inducing iPS cells include: (1) DMEM, DMEM/F12 or DME medium containing 10-15% FBS (wherein these media may further optionally contain LIF, penicillin/streptomycin, puromycin, L-glutamine, nonessential amino acids, β-mercaptoethanol, and the like); (2) a medium for ES cell culture containing bFGF or SCF, such as a medium for mouse ES cell culture (e.g., TX-WES medium (sold by Thromb-X)); and (3) a medium for primate ES cell culture (e.g., a medium for primate (human or monkey) ES cells (sold by ReproCELL, Kyoto, Japan), mTeSR-1).

Examples of culture methods are as follows. Somatic cells are brought into contact with nuclear reprogramming substances (DNAs, RNAs or proteins) on a DMEM or DMEM/F12 medium containing 10% FBS at 37° C. in the presence of 5% $CO_2$ and are cultured for about 4 to 7 days. Subsequently, the cells are reseeded on feeder cells (e.g., mitomycin C-treated STO cells or SNL cells). About 10 days after contact of a somatic cell with nuclear reprogramming substances, the cell is cultured on a bFGF-containing medium for primate ES cell culture. About 30-45 days or more after the contact, ES cell-like colonies can be formed. The resulting cells may also be cultured under conditions in which the oxygen concentration is as low as 5%-10% in order to increase the efficiency for inducing iPS cells.

Alternatively, said cells may be cultured on a DMEM medium containing 10% FBS, which medium may further optionally contain LIF, penicillin/streptomycin, puromycin, L-glutamine, nonessential amino acids, b-mercaptoethanol, and the like, on feeder cells (e.g., mitomycin C-treated STO cells or SNL cells). After about 25-30 days or more, ES cell-like colonies can be formed.

During the above culture, medium exchanges with a fresh medium are performed once a day from day 2 after the start of culture. In addition, the number of somatic cells used for nuclear reprogramming is not limited, but ranges from approximately $5 \times 10^3$ cells to approximately $5 \times 10^6$ cells per culture dish (100 $cm^2$).

When a DNA containing a drug resistance gene is used as a marker gene, cells expressing the marker gene can be selected by culturing the cells on a medium (i.e., a selective medium) containing such drug. Also, cells expressing the marker gene can be detected by observation with a fluorescence microscope when the marker gene is a fluorescent protein gene, by adding a luminescent substrate when the marker gene is a luminescent enzyme gene, or by adding a chromogenic substrate when the marker gene is a chromogenic enzyme gene.

The term "somatic cell" as used herein may refer to all cells other than germ cells from mammals (e.g., humans, mice, monkeys, pigs, and rats). Examples of such somatic cells include keratinizing epithelial cells (e.g., keratinizing epidermal cells), mucosal epithelial cells (e.g., epithelial cells of the surface layer of tongue), exocrine epithelial cells (e.g., mammary glandular cells), hormone-secreting cells (e.g., adrenal medullary cells), cells for metabolism and storage (e.g., hepatocytes), boundary-forming luminal epithelial cells (e.g., type I alveolar cells), luminal epithelial cells of internal tubules (e.g., vascular endothelial cells), ciliated cells having a carrying capacity (e.g., airway epithelial cells), cells for secretion to extracellular matrix (e.g., fibroblasts), contractile cells (e.g., smooth muscle cells), cells of blood and immune system (e.g., T lymphocytes), cells involved in sensation (e.g., rod cells), autonomic nervous system neurons (e.g., cholinergic neurons), sense organ and peripheral neuron supporting cells (e.g., satellite cells), nerve cells and glial cells of the central nervous system (e.g., astroglial cells), chromocytes (e.g., retinal pigment epithelial cells), and progenitor cells thereof (tissue progenitor cells). Without particular limitation concerning the degree of cell differentiation, the age of an animal from which cells are collected, or the like, both undifferentiated progenitor cells (also including somatic stem cells) and terminally-differentiated mature cells can be similarly used as origins for somatic cells in the present invention. Examples of undifferentiated progenitor cells include tissue stem cells (somatic stem cells) such as neural stem cells, hematopoietic stem cells, mesenchymal stem cells, and dental pulp stem cells.

In the present invention, mammals from which somatic cells are collected are not particularly limited and are preferably humans.

(E) Clone Embryo-Derived ES Cell Obtained by Nuclear Transplantation

The ntES cell is a clone embryo-derived ES cell prepared by nuclear transplantation techniques, having properties almost the same as those of fertilized egg-derived ES cells (T. Wakayama et al. (2001), Science, 292:740-743; S. Wakayama et al. (2005), Biol. Reprod., 72:932-936; J. Byrne et al. (2007), Nature, 450:497-502). Specifically, ntES (nuclear transfer ES) cells are established from the inner cell mass of a blastocyst from a clone embryo that is obtained via substitution of the nucleus of an unfertilized egg with the nucleus of a somatic cell. For preparation of ntES cells, nuclear transplantation techniques (J. B. Cibelli et al. (1998), Nat. Biotechnol., 16: 642-646) and the above ES cell preparation techniques are used in combination (Kiyoka Wakayama et al., (2008), Experimental Medicine, Vol. 26, No. 5 (Extra Number), pp. 47-52). Upon nuclear transplantation, the nucleus of a somatic cell is injected into a mammalian enucleated unfertilized egg and subsequently the resultant cell is cultured for several hours, so that the reprogramming can be carried out.

(F) Fusion Stem Cell

Fusion stem cells are prepared by fusing a somatic cell to an egg or ES cell, so that they have pluripotency similar to that of the ES cell to be fused thereto. Moreover, the fusion stem cells also have a gene peculiar to somatic cells (Tada M et al. Curr Biol. 11: 1553-8, 2001; Cowan C A et al. Science. 2005 Aug. 26; 309 (5739): 1369-73).

<Method for Inducing Differentiation into Intermediate Mesoderm Cells>

According to the present invention, a method comprising the following steps (A) and (B) can be used to induce the differentiation of pluripotent stem cells such as ES cells or iPS cells, into intermediate mesoderm cells.

In addition, reagents to be used in the method of the present invention are available substances, such as commercial items and substances described in documents.

The term "intermediate mesoderm cell" as used herein refers to a cell capable of differentiating into pronephros, mesonephros, mesonephric duct, metanephros, adrenal cortex, or genital gland, and preferably it refers to a cell expressing OSR1.

In the present invention, intermediate mesoderm cells obtained via induced differentiation may be provided as a cell population containing other cell species or as a purified cell population.

(A) Step of Culturing Cells in a Medium Containing Activin A and Wnt or a Functional Equivalent of Wnt This step can be performed using any of the two types of culture methods: a first method comprising forming a cell population (or a cell aggregate) or cell mass of human pluripotent stem cells during culture; or a second method comprising culturing human pluripotent stem cells that are substantially separated from each other during culture.

In the first method, human pluripotent stem cells are cultured by suspension culture in a medium containing Activin A and Wnt or a functional equivalent of Wnt, thereby forming a cell population or a cell mass. For the formation of a cell population or a cell mass, human pluripotent stem cells that have already formed a cell population may be once separated into small cell masses and then may be caused to reaggregate. Here, for separation into small cell masses, a cell mass may be finely separated by using a separation solution or mechanically. A preferable method comprises using a separation solution and then mechanically separating a cell mass into small masses. Examples of the separation solution to be used herein include a separation solution having protease activity and collagenase activity (e.g., a solution containing trypsin and collagenase, such as Accutase™ and Accumax™ (each of which is available from, for example, Funakoshi, Japan)) and a separation solution having collagenase activity alone. In this method, a separation solution having collagenase activity alone is preferably used as the separation solution.

In the second method, human pluripotent stem cells are substantially separated (or dissociated) from a cell population (or aggregate) or cell mass thereof by appropriate methods as described above and then cultured by adhesion culture using a medium containing Activin A and Wnt or a functional equivalent of Wnt. Here, the separated (or dissociated) pluripotent stem cells may be cultured by adhesion culture using a medium containing Activin A and Wnt or a functional equivalent of Wnt, after the cells may be cultured using a medium, which is used for culturing pluripotent stem cells, to 80% confluence for colony formation, or immediately after separation (or dissociation). Examples of a method for separation to be used herein include a mechanical method and a method using a separation solution having protease activity and collagenase activity (e.g., a solution containing trypsin and collagenase, such as Accutase™ and Accumax™) or using a separation solution having collagenase activity alone. Preferable examples of such methods include a method comprising dissociating cells using a separation solution having protease activity and collagenase activity and a method comprising dissociating cells using a separation solution having protease activity and collagenase activity and then mechanically and finely separating cells.

The first and the second methods will be further described as follows.

In the suspension culture, cells are cultured without being adhered to a culture dish. The suspension culture can be carried out using a culture dish that has not been artificially treated (e.g., by a coating-treatment with extracellular matrixex or the like) in order to improve its property of adhering to cells with cells, or that has been treated (e.g., by a coating-treatment using polyhydroxyethyl methacrylate (poly-HEMA)) to artificially suppress adhesion. However, the examples are not particularly limited to them. In the first method, a cell population (or cell mass) is formed by suspension culture of human pluripotent stem cells.

In adhesion culture, cells are cultured using a culture dish that has been treated with a coating agent. Examples of the coating agent include Matrigel™ (BD), collagen, gelatin, laminin, heparan sulfate proteoglycan, and entactin, or combinations thereof. The preferred coating agent is Matrigel™ or collagen. Wherein the collagen are selected from the group consisting of type I, type II, type III and type V collagen.

The medium for this step can be prepared using a medium to be used for culturing animal cells, as a basal medium. Examples of a basal medium include IMDM, Medium 199, Eagle's Minimum Essential Medium (EMEM), αMEM, Doulbecco's modified Eagle's Medium (DMEM), Ham's F12 medium, RPMI 1640 medium, Fischer's medium, and mixtures thereof. Preferably, the mixture of media is DMEM/F12 (1:1). Such medium may or may not contain serum. Where needed, the medium may contain one or more serum substitutes selected from, for example, albumin, transferrin, Knockout Serum Replacement (KSR) (which is a serum substitute for FBS upon culture of ES cells), N2 supplement (Invitrogen), B27 supplement (Invitrogen), fatty acids, insulin, procollagens, trace elements, 2-mercaptoethanol, and 3'-thiolglycerol, and may further contain one or more substances selected from, for example, lipids, amino acids, L-glutamine, GlutaMAX™ (Invitrogen), nonessential amino acids, vitamins, growth factors, antibiotics, antioxidants, pyruvate, buffering agents, inorganic salts, and substances equivalent thereto. Examples of preferable growth factors include Wnt1, Wnt3, Wnt3a, Wnt4, Wnt7a, TGF-β, Activin A, Nodal, BMP2, BMP4, BMP6, BMP7, and GDF. At least, in this step, Wnt3a and Activin A are desirably used as growth factors.

In the present invention, a functional equivalent of Wnt may be used instead of Wnt. The term "functional equivalent of Wnt" refers to a substance suppressing the formation of a complex of an Fz receptor and a ligand for LRP5/6 membrane protein, or a complex of β catenin and a molecule containing Axin, GSK3β, and APC (adenomatous polyposis coli). An example of such a substance is a Wnt agonist or a GSK3β inhibitor.

As used herein, the term "GSK3β inhibitor" is defined as a substance that inhibits the kinase activity (e.g., an ability to phosphorylate β-catenin) of a GSK (glycogen synthase kinase)-3β protein and many inhibitors are already known. Specific examples thereof include an indirubin derivative such as BIO (another name: GSK-3β inhibitor IX; 6-bromoindirubin-3'-oxime), a maleimide derivative such as SB216763 (3-(2,4-dichlorophenyl)-4-(1-methyl-1H-indole-3-yl)-1H-pyrrole-2,5-dione), a phenyl α bromomethylketone compound such as GSK-3β inhibitor VII (4-dibromo-acetophenone), and CHIR99021, i.e., 6-[(2-{[4-(2,4-dichlorophenyl)-5-(4-methylimidazole-2-yl)pyrimidine-2-yl]amino}ethyl)amino]pyridine-3-carbonitrile (WO1999/65897; CAS Number 252917-06-9), and, a cell membrane-permeable phosphorylation peptide such as L803-mts (another name: GSK-3β peptide inhibitor; Myr-N-GKEAP-PAPPQSpP-NH2), and derivatives thereof. These compounds are marketed by Calbiochem, Biomol, Stemgen, and the like and can be easily used. However, the examples thereof are not particularly limited thereto. Furthermore, an example of a Wnt agonist is 2-amino-4-(3,4-(methylenedioxy)benzylamino)-6-(3-methoxyphenyl)pyrimidine.

The concentration of Activin A or Wnt in a medium is not particularly limited and is preferably about 100 ng/ml or more, more preferably 100 ng/ml.

An example of preferable medium is a DMEM/Ham's F12 mixture containing 2% FBS, GlutaMAX™, penicillin, streptomycin, Wnt3a or GSK3β inhibitor (e.g., CHIR99021), and Activin A.

The temperature for culture ranges from about 30° C. to 40° C. and is preferably about 37° C., but the temperature is not limited thereto. Culture is carried out under an atmosphere containing air/$CO_2$. The $CO_2$ concentration preferably ranges from about 2% to 5%. The culture time ranges from 2 to 5 days for example, and is more preferably 2 days.

(B) Step of Culturing Cells Using a Medium Containing BMP and Wnt or a Functional Equivalent of Wnt In this step, the cell population after suspension culture, which is obtained in the previous step, can be directly cultured on an appropriate medium using a coated culture dish.

Examples of the coating agent include Matrigel™, collagen, gelatin, laminin, heparan sulfate proteoglycan, and entactin, or combinations thereof. A preferable example of the coating agent is Matrigel™, collagen, or gelatin. Wherein the collagen are selected from the group consisting of type I, type II, type III and type V collagen.

Alternatively, in this step, cells obtained by adhesion culture in the above step may be continuously cultured while the medium is exchanged with a fresh medium.

The medium usable in this step can be prepared using a medium for culturing animal cells as a basal medium. Examples of the basal medium include IMDM, Medium 199, Eagle's Minimum Essential Medium (EMEM), aMEM, Doulbecco's modified Eagle's Medium (DMEM), Ham's F12 medium, RPMI 1640 medium, Fischer's medium, and mixtures thereof. Preferable medium is DMEM. A serum-free medium is desirable. Where needed, the medium may contain one or more serum substitutes elected from, for example, albumin, transferrin, sodium selenite, ITS-X (Invitrogen) (containing insulin, transferrin, and sodium selenite), Knockout Serum Replacement (KSR) (which is a serum substitute for FBS upon culture of ES cells), N2 supplement (Invitrogen), B27 supplement (Invitrogen), fatty acids, insulin, procollagens, trace elements, 2-mercaptoethanol, and 3'-thiolglycerol, and may further contain one or more substances selected from, for example, lipids, amino acids, L-glutamine, GlutaMAX™, nonessential amino acids, vitamins, growth factors, antibiotics, antioxidants, pyruvate, buffering agent, inorganic salts, and GSK3β inhibitors. Examples of preferable growth factors include Wnt1 (e.g., NM_005430, NM_001204869), Wnt3 (e.g., NM_030753), Wnt3a (e.g., NM_033131 (SEQ ID NOs: 3 and 4), Wnt4 (e.g., NM_030761), Wnt7a (e.g., NM_004625), TGF-β (e.g., NM_000660, NM_001135599, NM_003238, NM_003239), Activin A (a disulfide-linked dimeric protein of inhibin beta A (NM_002192); e.g., human Activin A recombinant protein (eBioscience, Cat. No. 14-8993-62, etc.)), Nodal (e.g., NM_018055), BMP2 (e.g., NM_001200), BMP4 (e.g., NM_001202, NM_130850, NM_130851), BMP6 (e.g., NM_001718), BMP7 (e.g., NM_001719 (SEQ ID NOs: 1 and 2), and GDF (e.g., NM_001492, NM_016204, NM_020634, NM_000557, NM_001001557, NM_182828, NM_005259, NM_005260, NM_004962, NM_005811, NM_004864). In this step, at least Wnt3a and BMP7 can preferably be used as growth factors.

The concentration of BMP in the medium is not particularly limited and is preferably about 100 ng/ml or more and is more preferably 100 ng/ml.

An example of preferable medium is a DMEM/Ham's F12 mixed medium containing 10% KSR, GlutaMAX™, 2-mercaptoethanol, nonessential amino acids, penicillin, streptomycin, Wnt3a, and BMP7.

The culture temperature ranges from about 30° C. to 40° C., preferably about 37° C., but the temperature is not limited thereto. Culture is carried out under an atmosphere containing air/$CO_2$. The $CO_2$ concentration preferably ranges from about 2% to 5%. The culture time ranges from 4 to 21 days, for example. The culture time of step (B) after the first method of step (A) is from 14 to 18 days, preferably 16 days, for example. On the other hand, the culture time of step (B) after the second method of step (A) is from 7 to 10 days, preferably 8 days, for example. Medium exchange is desirably carried out every 3 days. Intermediate mesoderm cells are induced by this adhesion culture.

In the present invention, induction of differentiation into metanephric cells may be performed by further continuing adhesion culture.

<Kit for Inducing Differentiation into Intermediate Mesoderm Cells>

The present invention further provides a kit for inducing the differentiation of pluripotent stem cells into intermediate mesoderm cells.

The kit can comprise Activin A, Wnt or a functional equivalent thereof, and BMP, in different containers. The kit may further comprise culture media for said step (i) and said step (ii). Alternatively, the Activin A and the Wnt or a functional equivalent of Wnt may be contained in a culture medium, and/or the BMP and the Wnt or a functional equivalent of Wnt may be contained in a culture medium.

In the kit, the human pluripotent stem cell may be further comprised. The cell may be a human pluripotent stem cell having a foreign reporter gene in the chromosome, wherein the gene is expressed interlocked with the expression of endogenous OSR1. The reporter gene may be a DNA encoding a fluorescent protein, a luminescent protein, GUS, or LacZ, for example. Also, the pluripotent stem cell may be a human induced pluripotent (iPS) cell.

This kit may further comprise, in addition to the above components or elements, a cell-dissociation medium, and a coating agent for coating a culture dish, and optionally written procedures or instructions for induction of differentiation.

<Intermediate Mesoderm Cell>

The present invention provides intermediate mesoderm cells prepared by the above method for induction of differentiation.

Intermediate mesoderm cells can be identified using markers for intermediate mesoderm cells, such as OSR1, PAX2, WT1, EYA1, and SIX2.

<Human Pluripotent Stem Cell having Reporter Gene Within Chromosome>

Human pluripotent stem cells having a reporter gene in the chromosome, whose expression is interlocked with the expression of OSR1, can be produced by homologous recombination using a targeting vector. A typical example thereof is as follows.

Based on the nucleotide sequence information of a human OSR1 gene specified as NCBI Accession No. NM_145260, a targeting vector for homologous recombination can be constructed. The targeting vector may be constructed by designing nucleotide sequences on the vector, so that it has: a nucleic acid comprising the nucleotide sequence of an OSR1 gene itself on the chromosome or a nucleotide sequence partially deleted from the OSR1 gene on the chromosome; or a nucleic acid comprising a nucleotide sequence wherein the 5' side and the 3' side of a heterologous gene differing from the OSR1 gene are flanked by upstream and downstream nucleotide sequences of the OSR1 gene on the chromosome.

The targeting vector preferably comprises an appropriate marker gene for selection of cells into which the vector has been incorporated or a homologous recombinant cell of interest. As such marker genes, known drug resistance genes that are generally used for selection using drug resistance can be used, such as a neomycin resistance gene (neo), a diphtheria toxin A fragment gene (DT-A), a hygromycin resistance gene, an ampicillin resistance gene, a tetracycline resistance gene, a streptomycin resistance gene, and a herpes virus thymidine kinase gene (HSV-tk).

Also, the targeting vector may have a reporter gene at a position to be incorporated via homologous recombination onto the chromosome. In this case, for example, the translation frame of a reporter gene is preferably designed to be in agreement with the translation frame of the OSR1 gene, so that the sequence of the translation region of the OSR1 gene is partially or entirely deleted, substituted with another non-homologous nucleotide sequence, or inserted without deletion. Any reporter gene may be used, as long as it is generally used. Examples of such a reporter gene include DNA and the like encoding luminescent proteins such as *Escherichia coli* β-galactosidase (LacZ), β-gluconidase (GUS), and luciferase (Luc), fluorescent proteins such as a green fluorescent protein (GFP), aequorin, and taumarin.

The targeting vector for homologous recombination can be easily constructed by general DNA recombination techniques and specifically by general genetic engineering techniques appropriately using the above nucleic acid, marker gene, reporter gene, and the like for PCR and synthetic linker DNA, for example.

In an embodiment of the present invention, a targeting vector may be a BAC clone. Examples of preferable BAC clones include RP11-458J18, RP11-203M1, and RP11-802J2. When a BAC clone is used, for example, a marker gene or the like can be introduced into desired positions by the Red/ET homologous recombination method.

Subsequently, the targeting vector for homologous recombination is introduced into human pluripotent stem cells. The targeting vector can be introduced into the cells by methods known in the art. Examples of such methods include electroporation and microinjection.

In cells in which a targeting vector has been incorporated, recombination of a target gene on the chromosome, i.e. OSR1 gene, may take place between the targeting vector and one allele. Alternatively, the OSR1 gene may be recombined with 2 alleles. Specifically, a reporter gene or the like is introduced through incorporation of a nucleic acid region on vector flanked by homologous regions into the chromosome. The cells in which a mutation has thus been introduced can be selected based on the expression of the vector-derived marker gene. Moreover, among the thus selected cells, cells in which a mutation has been introduced into a desired position can be confirmed and selected by a PCR method, a Southern blotting method, or the like.

<Method for Producing Metanephric Cell>

The present invention further provides a method for producing a metanephric cell, comprising inducing intermediate mesoderm from a human pluripotent stem cell by the above-described method comprising steps (A) and (B) and then continuing the step (B) so as to produce the metanephric cell.

The culture conditions or the like for induction of intermediate mesoderm from human pluripotent stem cells that can be used herein are the same as those described above. Also, the culture conditions or the like for continuing the subsequent step (B) are also the same as those described above.

Culturing can be continued until metanephric cells that are mesenchymal cells can be obtained.

<Screening for an Inducer for Differentiation into Intermediate Mesoderm Cells>

Human pluripotent stem cells having a reporter gene in the chromosome, which gene is expressed interlocked with the expression of OSR1, can also be used for screening for an inducer of differentiation (which inducer is selected from, e.g., pharmaceutical compounds, solvents, low-molecular-weight substances, peptides, or polynucleotides) into intermediate mesoderm cells. For example, a candidate differentiation inducer, which is alone or in combination with any of other drugs, is brought into contact with the above-described human pluripotent stem cells having a reporter gene in the chromosome, whose expression is interlocked with the expression of OSR1. Evaluation can be made on the basis of change in expression levels of the reporter gene at such time. In the present invention, a drug that increases the expression level of a reporter gene can be identified as an inducer for differentiation into intermediate mesoderm. Preferably, a candidate substance is added to a medium for human pluripotent stem cells which have a reporter gene in the chromosome of OSR1 locus and have been adhered to a dish, and thus a substance capable of increasing an expression level of the reporter gene in the cells is selected.

EXAMPLES

The present invention will be further described in detail using examples as follows, but the scope of the present invention is not limited by these examples.

Example 1

Establishment of OSR1-GFP Knocked-In Human iPS Cell Line

Figure 1:
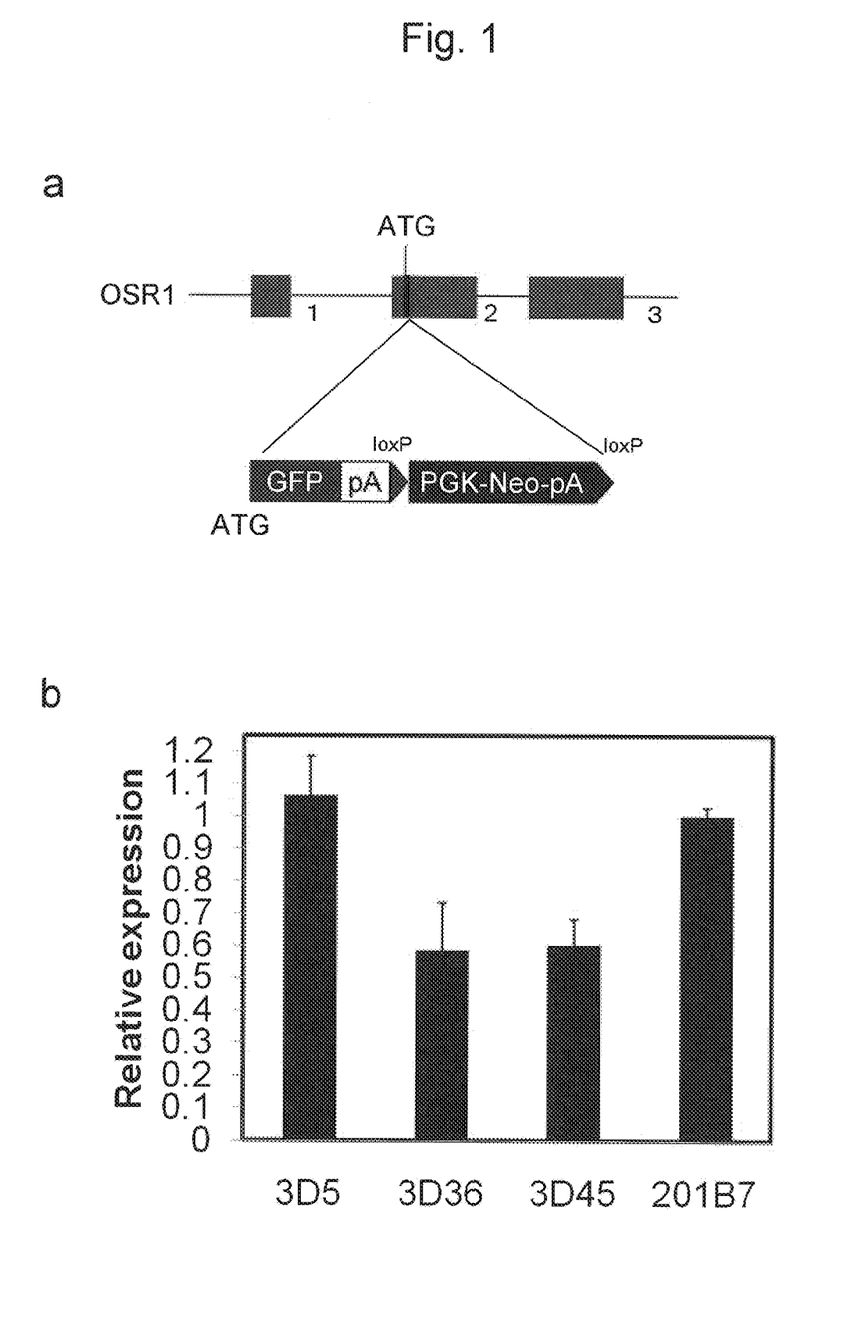
FIG. 1a shows a schematic diagram showing the knock-in of a GFP-PGK-Neo cassette into the OSR1 locus of a BAC clone (RP11-458J18). In this figure, OSR1 is odde-skipped related 1, ATG is an initiation codon, GFP is a DNA encoding green fluorescent protein, pA is a polyadenylation signal, PGK is 3-phosphoglycerate kinase, and Neo is neomycine resistance gene.
FIG. 1b shows a graph showing the results of quantification PCR analysis of genomic DNA for detecting around the initiation codon of OSR1 in each of the iPS cell lines after introduction of the modified BAC clone (i.e., 3D5, 3D36, 3D45, and control 201B7) for recombination. Note that the vertical axis value of 1 indicates two intact OSR1 loci, while 0.5 suggests one intact and one targeted locus.

Human iPS cell (201B7) received from Dr. Yamanaka at Kyoto University (Kyoto, Japan) was cultured by the known method (Takahashi K, et al. Cell. 131: 861-872, 2007). Subsequently, a GFP-PGK-Neo cassette was inserted downstream of the OSR1 initiation codon of a BAC clone (RP11-458J18) (BACPAC RESOURCES) using pRed/ET (Gene Bridges GmbH), so that a OSR1-GFP BAC transgene was prepared (FIG. 1a). Quantitative PCR was performed using as templates the chromosomes of about 130 iPS cell lines, into which the thus prepared modified BAC clone had been introduced, and primers designed to flank the initiation codon (former primer: 5'-GGATTGAGAAGCCACTGCAACT-3' (SEQ ID NO: 5) and reverse primer: 5'-CCGTTCACTGC-CTGAAGGA-3' (SEQ ID NO: 6)). It was confirmed that the amount of amplification products in each of four iPS cell lines was 1/2 the same in the case of control 201B7. Of these four cell lines, FIG. 1b shows the results for 3D36 and 3D45. As described above, an OSR1-GFP reporter iPS cell line expressing GFP interlocked with the expression of endogenous OSR1 was successfully established.

Example 2

Induction of Differentiation into Intermediate Mesoderm by Suspension Culture

The above prepared OSR1-GFP reporter iPS cell (3D36) was cultured to confluence using MEF as feeder cell. A collagenase solution (1 mg/ml) diluted with DMEM was added for dissociation. After the removal of the collagenase solution, DMEM/F12 containing GlutaMAX™ (Invitrogen), penicillin, streptomycin, and 2% FBS (Hyclone) was added, followed by pipetting. Subsequently, after the removal of the medium, cells were cultured by suspension culture in DMEM/F12 containing 100 ng/ml Wnt3a, 100 ng/ml ActivinA, GlutaMAX™ (Invitrogen), penicillin, streptomycin, and 2% FBS (Hyclone), thereby forming embryoid bodies (EB). After 2 days of suspension culture, EB was recovered and then adhesion culture was performed using DMEM/F12 containing 100 ng/ml Wnt3a, 100 ng/ml BMP7, 0.055 mM 2-mercaptoethanol, 0.1 mM nonessential amino acids, GlutaMAX™, penicillin, streptomycin, and 10% KSR (Invitrogen) in gelatin-coated dishes for 16 days. During adhesion culture, medium exchange was performed once every 3 days.

Figure 2:
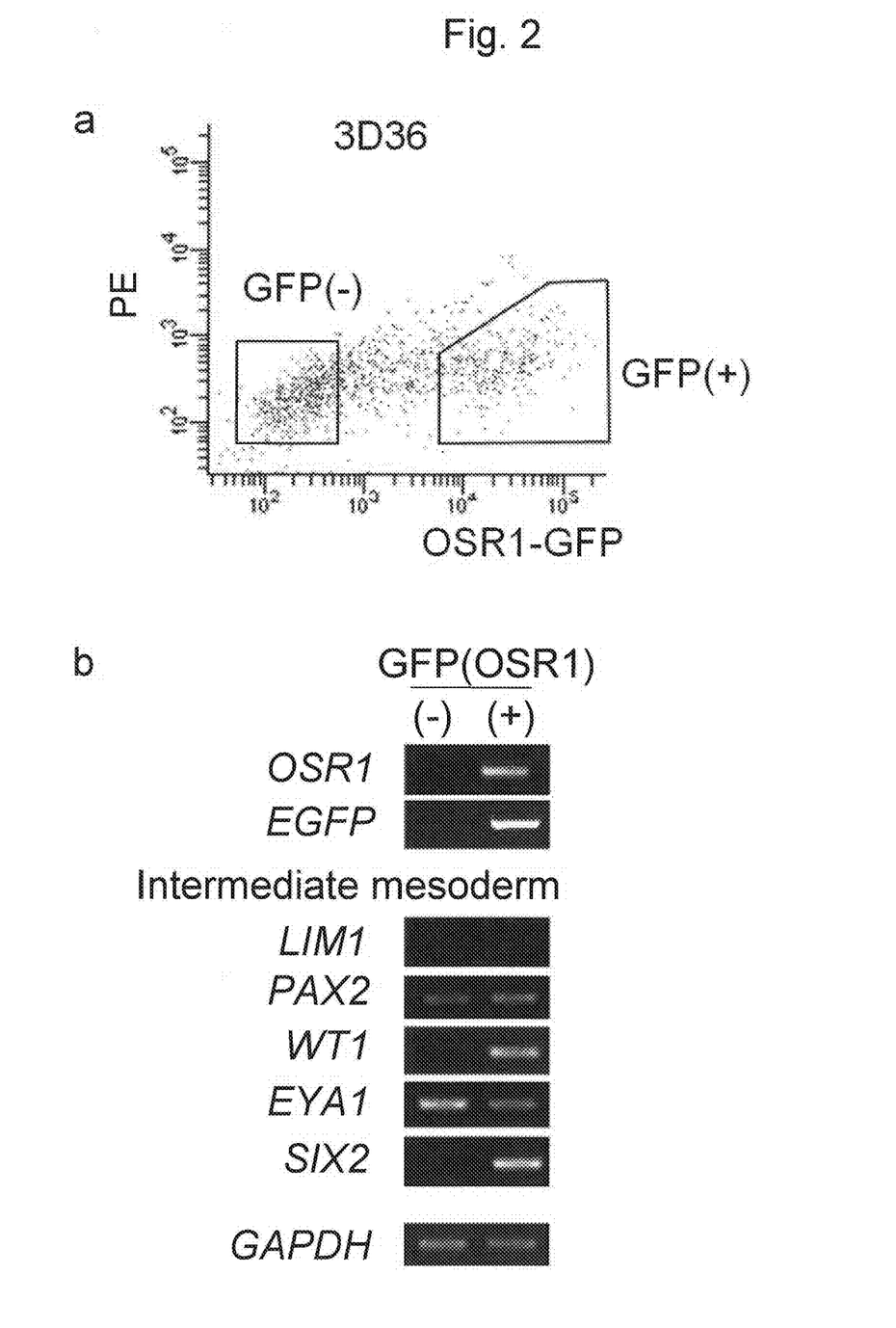
FIG. 2a shows the results of flow cytometry for evaluation of the GFP-positive iPS cell line 3D36 after differentiation induced by suspension culture. In this figure, the vertical axis indicates PE intensity and the horizontal axis indicates GFP intensity. PE is phycoerythrin.
FIG. 2b shows the results determined by RT-PCR of the expression levels of intermediate mesoderm marker genes in the iPS cell-derived OSR1-GFP-positive cell and in the OSR1-GFP-negative cell as a control.

FIG. 2a shows the results obtained by measuring the number of GFP-positive cells by flow cytometry after induced differentiation. It was thus confirmed that induction into GFP-positive cells (i.e., OSR1-positive cells) had been successful via the induction of differentiation described above.

Next, the expression of various differentiation marker genes in GFP-positive cells and GFP-negative cells after induction of differentiation was analyzed by PCR (FIG. 2b). It was confirmed by the results that the intermediate mesoderm marker genes, OSR1, WT1, EYA1, PAX2, and SIX2, had been expressed in GFP-positive cells.

Thus, OSR1-positive cells could be prepared from human iPS cells using the method described above.

Example 3

Induction of Differentiation into Intermediate Mesoderm by Adhesion Culture

The OSR1-GFP reporter iPS cell (3D36) obtained in Example 1 was cultured to confluence on 10-cm dishes having SNL cell (McMahon, A. P. and Bradley, A. (1990) Cell 62; 1073-1085) as feeder cell. A CTK solution (0.25% trypsin, 0.1% collagenase IV, 20% KSR, and 1 mM $CaCl_2$ containing PBS) was added for dissociation. Subsequently, the cells were added to and adhered to each well of a 24-well Matrigel™ (BD)-coated dish, in an amount of 1/24 relative to all the collected cells. The cells were cultured to confluence on a medium containing bFGF for primate ES cells (ReproCELL, Japan). Medium was exchanged with DMEM/F12 containing 100 ng/ml Wnt3a, 100 ng/ml ActivinA, GlutaMAX™ (Invitrogen), penicillin, streptomycin, and 2% FBS (Hyclone) and then cells were cultured for 2 days. Furthermore, the medium was exchanged with DMEM/F12 containing 100 ng/ml Wnt3a, 100 ng/ml BMP7, 0.055 mM 2-mercaptoethanol, 0.1 mM nonessential amino acid, GlutaMAX™, penicillin, streptomycin, and 10% KSR (Invitrogen), and then cells were cultured for 16 days. During culture, medium exchange was performed once every 3 days. After culture, cells were analyzed by FACS using GFP expression as an indicator, so that the presence of GFP-positive cells was confirmed.

Example 4

Figure 3:
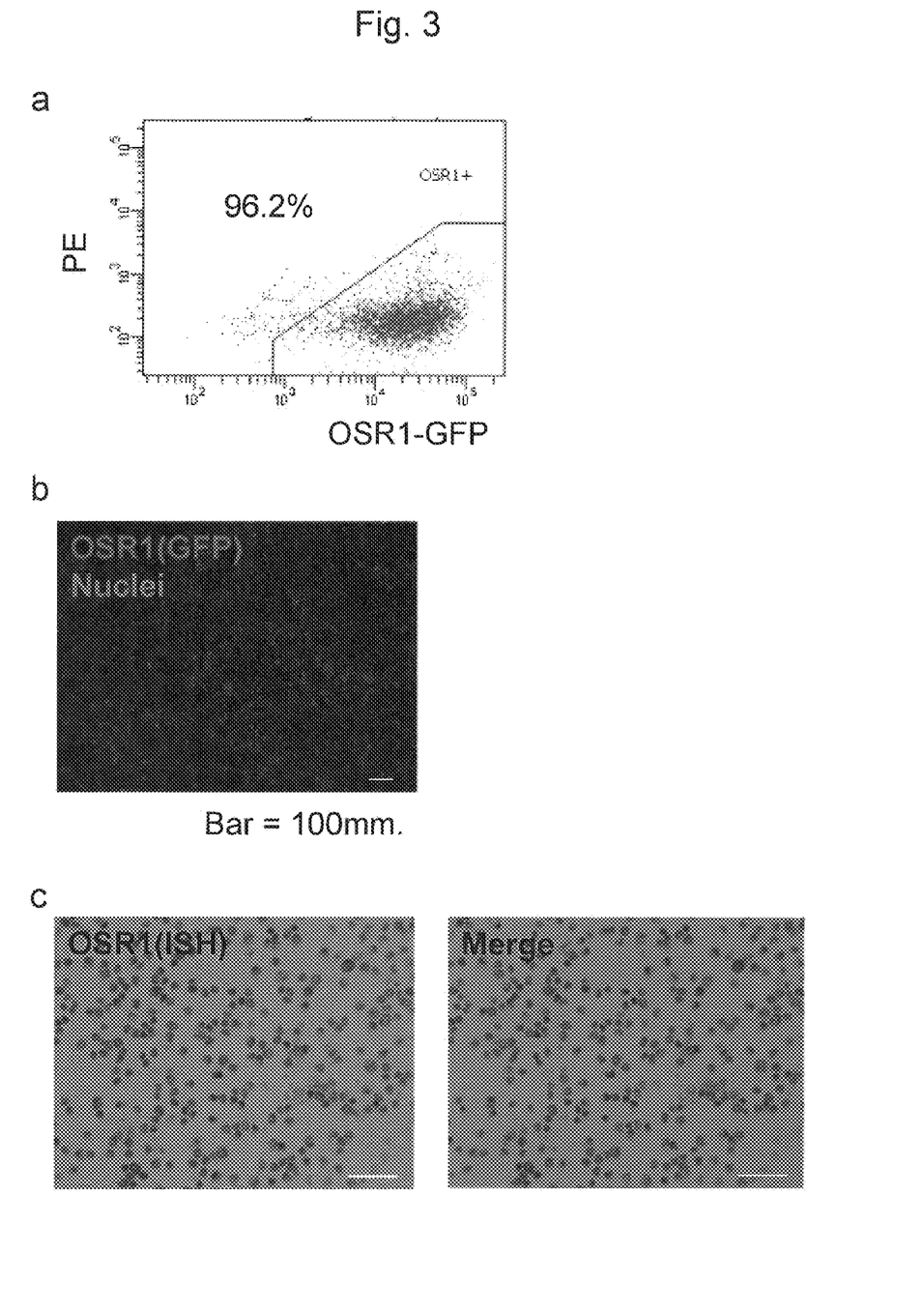
FIG. 3a shows the results of flow cytometry for evaluation of the GFP-positive cell line 3D45 after differentiation induced by separation culture.
FIG. 3b shows a fluorescence microscopic image obtained by nuclear staining with GFP and DAPI (4',6-diamino-2-phenylindole).
FIG. 3c shows a staining image of in situ hybridization (ISH) for OSR1 (left) and a merged image with the nuclear staining with DAPI (right).

Induction of Differentiation into Intermediate Mesoderm by Dissociation and Adhesion Culture The OSR1-GFP reporter iPS cell (3D45) obtained in Example 1 was cultured to confluence on 10-cm dishes having MEF as feeder cell. A CTK solution was added for dissociation. Furthermore, Accutase™ was added and then cells were dissociated by pipetting. DMEM/F12 containing GlutaMAX™, penicillin, streptomycin, and 2% FBS was added to stop the enzymatic reaction, followed by further pipetting. After the removal of the medium by centrifugation, cells were cultured for 2 days in Collagen I-coated 24-well plates having DMEM/F12 containing 10 μM Y27632, 100 ng/ml Activin A, 3 μM CHIR99021, GlutaMAX™, penicillin, streptomycin, and 2% FBS. Subsequently, the medium was exchanged with DMEM/F12 containing 100 ng/ml BMP7, 3 μM CHIR99021, 0.055 mM 2-mercaptoethanol, 0.1 mM nonessential amino acids, GlutaMAX™, penicillin, streptomycin, and 10% KSR and then cells were cultured for 8 days. During culture, medium exchange was performed once every 3 days. After culture, cells were analyzed by FACS using GFP expression as an indicator and then evaluated by fluorescence microscopy after immunostaining with an anti-GFP antibody, so that GFP-positive cells were confirmed (FIG. 3a and FIG. 3b). Cells were further evaluated by in situ hybridization for OSR1. As a result, OSR1 expression was confirmed in many cells after induction of differentiation (FIG. 3c).

INDUSTRIAL APPLICABILITY

The present invention makes it possible to prepare intermediate mesoderm cells from pluripotent stem cells such as ES cells or iPS cells. Intermediate mesoderm is very useful since it can induce the differentiation of pluripotent stem cells into cells which can be used in the field of regenerative medicine for treating renal diseases.

---

The invention claimed is:

1. A method for producing an intermediate mesoderm cell from a human pluripotent stem cell, comprising the following steps (i) and (ii) of:
   (i) culturing the human pluripotent stem cell in a medium containing Activin A and Wnt or a functional equivalent of Wnt, and then
   (ii) culturing the cell obtained in the step (i) in a medium containing BMP and Wnt or a functional equivalent of Wnt, and
   (iii) obtaining intermediate mesoderm cells,
   wherein the culture in the step (i) is performed for a culture period ranging from 2 to 5 days, and
   wherein the intermediate mesoderm cell is an OSR1-positive cell and is identified by detection of one or more markers selected from the group consisting of: PAX2, WT1, EYA1, and SIX2.

2. The method of claim 1, wherein in the culture of the step (i), the human pluripotent stem cell is cultured in suspension to form a cell population or cell mass of the human pluripotent stem cell, and in the culture of the step (ii), the cell population or the cell mass is subjected to adhesion culture, thereby forming the intermediate mesoderm cell.

3. The method of claim 1, further comprising, in the culture of the step (i), substantially separating the cell population or cell mass of human pluripotent stem cell into respective cells.

4. The method of claim 3, wherein step (i) further comprises adhering the separated cells to a Matrigel™-coated dish or a collagen-coated dish and then culturing the cells.

5. The method of claim 1, wherein in the step (i), the medium further contains fetal bovine serum (FBS).

6. The method of claim 1, wherein in the step (ii), the medium further contains a knockout serum replacement (KSR).

7. The method of claim 1, wherein the Wnt is Wnt3a.

8. The method of claim 1, wherein the functional equivalent of Wnt is a GSK3β inhibitor.

9. The method of claim 8, wherein the GSK3β inhibitor is CHIR99021.

10. The method of claim 1, wherein the BMP is BMP7.

11. The method of claim 2, wherein the culture in the step (ii) is performed for a culture period ranging from 14 to 18 days.

12. The method of claim 3, wherein the culture in the step (ii) is performed for a culture period ranging from 7 to 10 days.

13. The method of claim 1, wherein the human pluripotent stem cell is a human iPS cell or a human ES cell.

14. The method of claim 1, wherein the human pluripotent stem cell has a foreign reporter gene in the chromosome, wherein expression of the gene is interlocked with the expression of endogenous OSR1.

15. The method of claim 14, wherein the reporter gene is a DNA encoding a fluorescent protein, a luminescent protein, GUS, or LacZ.

16. The method of claim 14, wherein the pluripotent stem cell is a human iPS cell.

* * * * *

SEQUENCE LISTING

```
<160> NUMBER OF SEQ ID NOS: 6

<210> SEQ ID NO 1
<211> LENGTH: 4049
<212> TYPE: DNA
<213> ORGANISM: Homo sapiens
<220> FEATURE:
<221> NAME/KEY: CDS
<222> LOCATION: (530)..(1825)

<400> SEQUENCE: 1
agcgcgtacc actctggcgc tcccgaggcg gcctcttgtg cgatccaggg cgcacaaggc      60
tgggagagcg ccccggggcc cctgctatcc gcgccggagg ttggaagagg gtgggttgcc     120
gccgcccgag ggcgagagcg ccagaggagc gggaagaagg agcgctcgcc cgcccgcctg     180
cctcctcgct gcctccccgg cgttggctct ctggactcct aggcttgctg gctgctcctc     240
ccacccgcgc ccgcctcctc actcgccttt tcgttcgccg gggctgcttt ccaagccctg     300
cggtgcgccc gggcgagtgc ggggcgaggg gcccggggcc agcaccgagc aggggcggg      360 ggtccgggca gagcgcggcc ggccggggag gggccatgtc tggcgcgggc gcagcggggc     420
ccgtctgcag caagtgaccg agcggcgcgg acggccgcct gccccctctg ccacctgggg     480
cggtgcgggc ccggagcccg gagcccgggt agcgcgtaga gccggcgcg atg cac gtg    538
                                                    Met His Val
                                                     1
```
```
cgc tca ctg cga gct gcg gcg ccg cac agc ttc gtg gcg ctc tgg gca     586
Arg Ser Leu Arg Ala Ala Ala Pro His Ser Phe Val Ala Leu Trp Ala
      5                  10                  15 ccc ctg ttc ctg ctg cgc tcc gcc ctg gcc gac ttc agc ctg gac aac     634
Pro Leu Phe Leu Leu Arg Ser Ala Leu Ala Asp Phe Ser Leu Asp Asn
 20                  25                  30                  35 gag gtg cac tcg agc ttc atc cac cgg cgc ctc cgc agc cag gag cgg     682
Glu Val His Ser Ser Phe Ile His Arg Arg Leu Arg Ser Gln Glu Arg
                  40                  45                  50 cgg gag atg cag cgc gag atc ctc tcc att ttg ggc ttg ccc cac cgc     730
Arg Glu Met Gln Arg Glu Ile Leu Ser Ile Leu Gly Leu Pro His Arg
             55                  60                  65 ccg cgc ccg cac ctc cag ggc aag cac aac tcg gca ccc atg ttc atg     778
Pro Arg Pro His Leu Gln Gly Lys His Asn Ser Ala Pro Met Phe Met
         70                  75                  80 ctg gac ctg tac aac gcc atg gcg gtg gag gag ggc ggg ggg ccc ggc     826
Leu Asp Leu Tyr Asn Ala Met Ala Val Glu Glu Gly Gly Gly Pro Gly
     85                  90                  95 ggc cag ggc ttc tcc tac ccc tac aag gcc gtc ttc agt acc cag ggc     874
Gly Gln Gly Phe Ser Tyr Pro Tyr Lys Ala Val Phe Ser Thr Gln Gly
100                 105                 110                 115
```

-continued

| | | |
|---|---|---|
| ccc cct ctg gcc agc ctg caa gat agc cat ttc ctc acc gac gcc gac<br>Pro Pro Leu Ala Ser Leu Gln Asp Ser His Phe Leu Thr Asp Ala Asp<br>120 125 130 | 922 | |
| atg gtc atg agc ttc gtc aac ctc gtg gaa cat gac aag gaa ttc ttc<br>Met Val Met Ser Phe Val Asn Leu Val Glu His Asp Lys Glu Phe Phe<br>135 140 145 | 970 | |
| cac cca cgc tac cac cat cga gag ttc cgg ttt gat ctt tcc aag atc<br>His Pro Arg Tyr His His Arg Glu Phe Arg Phe Asp Leu Ser Lys Ile<br>150 155 160 | 1018 | |
| cca gaa ggg gaa gct gtc acg gca gcc gaa ttc cgg atc tac aag gac<br>Pro Glu Gly Glu Ala Val Thr Ala Ala Glu Phe Arg Ile Tyr Lys Asp<br>165 170 175 | 1066 | |
| tac atc cgg gaa cgc ttc gac aat gag acg ttc cgg atc agc gtt tat<br>Tyr Ile Arg Glu Arg Phe Asp Asn Glu Thr Phe Arg Ile Ser Val Tyr<br>180 185 190 195 | 1114 | |
| cag gtg ctc cag gag cac ttg ggc agg gaa tcg gat ctc ttc ctg ctc<br>Gln Val Leu Gln Glu His Leu Gly Arg Glu Ser Asp Leu Phe Leu Leu<br>200 205 210 | 1162 | |
| gac agc cgt acc ctc tgg gcc tcg gag gag ggc tgg ctg gtg ttt gac<br>Asp Ser Arg Thr Leu Trp Ala Ser Glu Glu Gly Trp Leu Val Phe Asp<br>215 220 225 | 1210 | |
| atc aca gcc acc agc aac cac tgg gtg gtc aat ccg cgg cac aac ctg<br>Ile Thr Ala Thr Ser Asn His Trp Val Val Asn Pro Arg His Asn Leu<br>230 235 240 | 1258 | |
| ggc ctg cag ctc tcg gtg gag acg ctg gat ggg cag agc atc aac ccc<br>Gly Leu Gln Leu Ser Val Glu Thr Leu Asp Gly Gln Ser Ile Asn Pro<br>245 250 255 | 1306 | |
| aag ttg gcg ggc ctg att ggg cgg cac ggg ccc cag aac aag cag ccc<br>Lys Leu Ala Gly Leu Ile Gly Arg His Gly Pro Gln Asn Lys Gln Pro<br>260 265 270 275 | 1354 | |
| ttc atg gtg gct ttc ttc aag gcc acg gag gtc cac ttc cgc agc atc<br>Phe Met Val Ala Phe Phe Lys Ala Thr Glu Val His Phe Arg Ser Ile<br>280 285 290 | 1402 | |
| cgg tcc acg ggg agc aaa cag cgc agc cag aac cgc tcc aag acg ccc<br>Arg Ser Thr Gly Ser Lys Gln Arg Ser Gln Asn Arg Ser Lys Thr Pro<br>295 300 305 | 1450 | |
| aag aac cag gaa gcc ctg cgg atg gcc aac gtg gca gag aac agc agc<br>Lys Asn Gln Glu Ala Leu Arg Met Ala Asn Val Ala Glu Asn Ser Ser<br>310 315 320 | 1498 | |
| agc gac cag agg cag gcc tgt aag aag cac gag ctg tat gtc agc ttc<br>Ser Asp Gln Arg Gln Ala Cys Lys Lys His Glu Leu Tyr Val Ser Phe<br>325 330 335 | 1546 | |
| cga gac ctg ggc tgg cag gac tgg atc atc gcg cct gaa ggc tac gcc<br>Arg Asp Leu Gly Trp Gln Asp Trp Ile Ile Ala Pro Glu Gly Tyr Ala<br>340 345 350 355 | 1594 | |
| gcc tac tac tgt gag ggg gag tgt gcc ttc cct ctg aac tcc tac atg<br>Ala Tyr Tyr Cys Glu Gly Glu Cys Ala Phe Pro Leu Asn Ser Tyr Met<br>360 365 370 | 1642 | |
| aac gcc acc aac cac gcc atc gtg cag acg ctg gtc cac ttc atc aac<br>Asn Ala Thr Asn His Ala Ile Val Gln Thr Leu Val His Phe Ile Asn<br>375 380 385 | 1690 | |
| ccg gaa acg gtg ccc aag ccc tgc tgt gcg ccc acg cag ctc aat gcc<br>Pro Glu Thr Val Pro Lys Pro Cys Cys Ala Pro Thr Gln Leu Asn Ala<br>390 395 400 | 1738 | |
| atc tcc gtc ctc tac ttc gat gac agc tcc aac gtc atc ctg aag aaa<br>Ile Ser Val Leu Tyr Phe Asp Asp Ser Ser Asn Val Ile Leu Lys Lys<br>405 410 415 | 1786 | |
| tac aga aac atg gtg gtc cgg gcc tgt ggc tgc cac tag ctcctccgag<br>Tyr Arg Asn Met Val Val Arg Ala Cys Gly Cys His<br>420 425 430 | 1835 | |

```
aattcagacc ctttggggcc aagttttcct ggatcctcca ttgctcgcct tggccaggaa      1895
ccagcagacc aactgccttt tgtgagacct tcccctccct atccccaact ttaaaggtgt      1955
gagagtatta ggaaacatga gcagcatatg gcttttgatc agttttcag tggcagcatc       2015
caatgaacaa gatcctacaa gctgtgcagg caaaacctag caggaaaaaa aaacaacgca      2075
taaagaaaaa tggccgggcc aggtcattgg ctgggaagtc tcagccatgc acggactcgt     2135
ttccagaggt aattatgagc gcctaccagc caggccaccc agccgtggga ggaaggggc       2195
gtggcaaggg gtgggcacat tggtgtctgt gcgaaaggaa aattgacccg gaagttcctg     2255
taataaatgt cacaataaaa cgaatgaatg aaaatggtta ggacgttaca gatatatttt     2315
cctaaacaat ttatccccat ttctcggttt atcctgatgc gtaaacagaa gctgtgtcaa     2375
gtggagggcg gggaggtccc tctccattcc ctacagtttt catcctgagg cttgcagagg     2435
cccagtgttt accgaggttt gcccaaatcc aagatctagt gggaggggaa agagcaaatg    2495
tctgctccga ggaggcggt gtgttgatct ttggaggaaa aatatgttct gttgttcagc     2555
tggatttgcc gtggcagaaa tgaaactagg tgtgtgaaat acccgcagac atttgggatt    2615
ggcttttcac ctcgccccag tggtagtaaa tccatgtgaa attgcagagg ggacaaggac     2675
agcaagtagg atggaacttg caactcaacc ctgttgttaa gaagcaccaa tgggccgggc    2735
acagtagctc ccacctgtaa tcccagcact tgggaggct gaggtgggcg gatcatttga     2795
ggtcaggagt tcgagaccag cctggccaac atggtgaaac cccatctcta ctaaaaatac   2855
aaaaattagc cgggcatggt ggcacgcacc tgtaatccca gctactctgg aggctgaggc    2915
aggagaattg cttgaacccc agaggtggag gttgcagtga gccaagatcg tcccactgca    2975
ctccagcttg ggtgacaaaa caagactcca tctcaaaaga aaaaaaaac agcaccaatg     3035
aagcctagtt ctccacggga gtggggtgag caggagcact gcacatcgcc ccagtggacc    3095
ctctggtctt tgtctgcagt ggcattccaa ggctgggccc tggcaagggc acccgtggct    3155
gtctcttcat ttgcagaccc tgatcagaag tctctgcaaa caaatttgct ccttgaatta    3215
agggggagat ggcataatag gaggtctgat gggtgcagga tgtgctggac ttacattgca    3275
aatagaagcc ttgttgaggg tgacatccta accaagtgtc ccgatttgga ggtggcattt    3335
ctgacgtggc tcttggtgta agcctgcctt gccttggctg gtgagtccca taaatagtat    3395
gcactcagcc tccggccaca aacacaaggc ctaggggagg gctagactgt ctgcaaacgt    3455
tttctgcatc tgtaaagaaa acaaggtgat cgaaaactgt ggccatgtgg aacccggtct   3515
tgtgggggac tgtttctcca tcttgactca gacagttcct ggaaacaccg gggctctgtt    3575
tttattttct ttgatgtttt tcttctttag tagcttgggc tgcagcctcc actctctagt    3635
cactggggag gagtattttt tgttatgttt ggtttcattt gctggcagag ctggggcttt    3695
ttgtgtgatc cctcttggtg tgagtttct gacccaacca gcctctggtt agcatcattt    3755
gtacatttaa acctgtaaat agttgttaca aagcaaagag attatttatt tccatccaaa   3815
gctcttttga acacccccc cccctttaatc cctcgttcag gacgatgagc ttgctttcct    3875
tcaacctgtt tgttttctta tttaagacta tttattaatg gttggaccaa tgtactcaca    3935
gctgttgcgt cgagcagtcc ttagtgaaaa ttctgtataa atagacaaaa tgaaaagggt    3995
ttgaccttgc aataaaagga gacgtttggt tctggcaaaa aaaaaaaaaa aaaa          4049
```

<210> SEQ ID NO 2
<211> LENGTH: 431
<212> TYPE: PRT

<213> ORGANISM: Homo sapiens

<400> SEQUENCE: 2

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

```
Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 2988
<212> TYPE: DNA
<213> ORGANISM: Homo sapiens
<220> FEATURE:
<221> NAME/KEY: CDS
<222> LOCATION: (108)..(1166)

<400> SEQUENCE: 3
gcaggagggc ccagcgacgc cgccgcgcca gctcccaggg cccggccccc ccggcgctc      60 acgctctcgg ggcggactcc cggccctccg cgccctctcg cgcggcg atg gcc cca     116
                                                    Met Ala Pro
                                                    1 ctc gga tac ttc tta ctc ctc tgc agc ctg aag cag gct ctg ggc agc     164
Leu Gly Tyr Phe Leu Leu Leu Cys Ser Leu Lys Gln Ala Leu Gly Ser
    5                   10                  15 tac ccg atc tgg tgg tcg ctg gct gtt ggg cca cag tat tcc tcc ctg     212
Tyr Pro Ile Trp Trp Ser Leu Ala Val Gly Pro Gln Tyr Ser Ser Leu
20                  25                  30                  35 ggc tcg cag ccc atc ctg tgt gcc agc atc ccg ggc ctg gtc ccc aag     260
Gly Ser Gln Pro Ile Leu Cys Ala Ser Ile Pro Gly Leu Val Pro Lys
                40                  45                  50 cag ctc cgc ttc tgc agg aac tac gtg gag atc atg ccc agc gtg gcc     308
Gln Leu Arg Phe Cys Arg Asn Tyr Val Glu Ile Met Pro Ser Val Ala
            55                  60                  65 gag ggc atc aag att ggc atc cag gag tgc cag cac cag ttc cgc ggc     356
Glu Gly Ile Lys Ile Gly Ile Gln Glu Cys Gln His Gln Phe Arg Gly
        70                  75                  80 cgc cgg tgg aac tgc acc acc gtc cac gac agc ctg gcc atc ttc ggg     404
Arg Arg Trp Asn Cys Thr Thr Val His Asp Ser Leu Ala Ile Phe Gly
    85                  90                  95 ccc gtg ctg gac aaa gct acc agg gag tcg gcc ttt gtc cac gcc att     452
Pro Val Leu Asp Lys Ala Thr Arg Glu Ser Ala Phe Val His Ala Ile
100                 105                 110                 115 gcc tca gcc ggt gtg gcc ttt gca gtg aca cgc tca tgt gca gaa ggc     500
Ala Ser Ala Gly Val Ala Phe Ala Val Thr Arg Ser Cys Ala Glu Gly
                120                 125                 130 acg gcc gcc atc tgt ggc tgc agc agc cgc cac cag ggc tca cca ggc     548
Thr Ala Ala Ile Cys Gly Cys Ser Ser Arg His Gln Gly Ser Pro Gly
            135                 140                 145 aag ggc tgg aag tgg ggt ggc tgt agc gag gac atc gag ttt ggt ggg     596
Lys Gly Trp Lys Trp Gly Gly Cys Ser Glu Asp Ile Glu Phe Gly Gly
        150                 155                 160 atg gtg tct cgg gag ttc gcc gac gcc cgg gag aac cgg cca gat gcc     644
Met Val Ser Arg Glu Phe Ala Asp Ala Arg Glu Asn Arg Pro Asp Ala
    165                 170                 175 cgc tca gcc atg aac cgc cac aac aac gag gct ggg cgc cag gcc atc     692
Arg Ser Ala Met Asn Arg His Asn Asn Glu Ala Gly Arg Gln Ala Ile
180                 185                 190                 195 gcc agc cac atg cac ctc aag tgc aag tgc cac ggg ctg tcg ggc agc     740
Ala Ser His Met His Leu Lys Cys Lys Cys His Gly Leu Ser Gly Ser
                200                 205                 210 tgc gag gtg aag aca tgc tgg tgg tcg caa ccc gac ttc cgc gcc atc     788
Cys Glu Val Lys Thr Cys Trp Trp Ser Gln Pro Asp Phe Arg Ala Ile
            215                 220                 225
```

```
ggt gac ttc ctc aag gac aag tac gac agc gcc tcg gag atg gtg gtg      836
Gly Asp Phe Leu Lys Asp Lys Tyr Asp Ser Ala Ser Glu Met Val Val
        230                 235                 240 gag aag cac cgg gag tcc cgc ggc tgg gtg gag acc ctg cgg ccg cgc      884
Glu Lys His Arg Glu Ser Arg Gly Trp Val Glu Thr Leu Arg Pro Arg
    245                 250                 255 tac acc tac ttc aag gtg ccc acg gag cgc gac ctg gtc tac tac gag      932
Tyr Thr Tyr Phe Lys Val Pro Thr Glu Arg Asp Leu Val Tyr Tyr Glu
260                 265                 270                 275 gcc tcg ccc aac ttc tgc gag ccc aac cct gag acg ggc tcc ttc ggc      980
Ala Ser Pro Asn Phe Cys Glu Pro Asn Pro Glu Thr Gly Ser Phe Gly
                280                 285                 290 acg cgc gac cgc acc tgc aac gtc agc tcg cac ggc atc gac ggc tgc     1028
Thr Arg Asp Arg Thr Cys Asn Val Ser Ser His Gly Ile Asp Gly Cys
            295                 300                 305 gac ctg ctg tgc tgc ggc cgc ggc cac aac gcg cga gcg gag cgg cgc     1076
Asp Leu Leu Cys Cys Gly Arg Gly His Asn Ala Arg Ala Glu Arg Arg
        310                 315                 320 cgg gag aag tgc cgc tgc gtg ttc cac tgg tgc tgc tac gtc agc tgc     1124
Arg Glu Lys Cys Arg Cys Val Phe His Trp Cys Cys Tyr Val Ser Cys
    325                 330                 335 cag gag tgc acg cgc gtc tac gac gtg cac acc tgc aag tag              1166
Gln Glu Cys Thr Arg Val Tyr Asp Val His Thr Cys Lys
340                 345                 350 gcaccggccg cggctccccc tggacggggc gggccctgcc tgagggtggg cttttccctg    1226
ggtggagcag gactcccacc taaacggggc agtactcctc cctgggggcg ggactcctcc    1286
ctgggggtgg ggctcctacc tggggcagaa actcctacct gaaggcaggg ctcctccctg    1346
gagctagtgt ctcctctctg gtggctgggc tgctcctgaa tgaggcggag ctccaggatg    1406
gggaggggct ctgcgttggc ttctccctgg gacggggct ccctggaca gaggcggggc      1466 tacagattgg gcgggcttc tcttgggtgg gacagggctt ctcctgcggg gcgaggccc      1526 ctcccagtaa gggcgtggct ctgggtgggc gggcactag gtaggcttct acctgcaggc    1586
ggggctcctc ctgaaggagg cggggctcta ggatggggca cggctctggg gtaggctgct   1646
ccctgagggc ggagcgcctc cttaggagtg gggttttatg gtggatgagg cttcttcctg    1706 gatgggcag agcttctcct gaccagggca aggccccttc cacggggct gtggctctgg      1766 gtgggcgtgg cctgcatagg ctccttcctg tgggtgggc ttctctggga ccaggctcca    1826
atggggcggg gcttctctcc gcgggtggga ctcttccctg ggaaccgccc tcctgattaa    1886
ggcgtggctt ctgcaggaat cccggctcca gagcaggaaa ttcagcccac cagccacctc    1946
atccccaacc ccctgtaagg ttccatccac ccctgcgtcg agctgggaag gttccatgaa    2006
gcgagtcggg tccccaaccc gtgccctgg gatccgaggg cccctctcca gcgcctggc     2066 tttggaatgc tccaggcgcg ccgacgcctg tgccacccct tcctcagcct ggggtttgac    2126
cacccacctg accaggggcc ctacctgggg aaagcctgaa gggcctccca gcccccaacc   2186
ccaagaccaa gcttagtcct gggagaggac agggacttcg cagaggcaag cgaccgaggc   2246
cctcccaaag aggcccgccc tgccggggct cccacaccgt caggtactcc tgccagggaa    2306
ctggcctgct gcgccccagg cccgccccgt ctctgtctg tcagctgcg ccccttctt       2366 tgcagctgcc cagcccctcc tccctgccct cgggtctccc cacctgcact ccatccagct    2426
acaggagaga tagaagcctc tcgtcccgtc cctcccttc ctcgcctgt ccacagcccc      2486 ttaagggaaa ggtaggaaga gaggtccagc ccccaggct gccagagct gctggtctca      2546 tttgggggcg ttcggaggt ttgggggca tcaaccccc gactgtgctg ctcgcgaagg       2606
```

```
tcccacagcc ctgagatggg ccggccccct tcctggcccc tcatggcggg actggagaaa    2666
tggtccgctt tcctggagcc aatgccccgg cccctcctga ctcatccgcc tggcccggga    2726
atgaatgggg aggccgctga acccacccgg cccatatccc tggttgcctc atggccagcg    2786
cccctcagcc tctgccactg tgaaccggct cccacccctca aggtgcgggg agaagaagcg    2846
gccaggcggg gcgcccccaag agcccaaaag agggcacacc gccatcctct gcctcaaatt    2906
ctgcgttttt ggttttaatg ttatatctga tgctgctata tccactgtcc aacggagtta    2966
gacgaaaaaa aaaaaaaaaa aa                                             2988
```

<210> SEQ ID NO 4
<211> LENGTH: 352
<212> TYPE: PRT
<213> ORGANISM: Homo sapiens

<400> SEQUENCE: 4

```
Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
 50                  55                  60

Ser Val Ala Glu Gly Ile Lys Ile Gly Ile Gln Glu Cys Gln His Gln
 65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
    290                 295                 300
```

-continued

```
Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
ggattgagaa gccactgcaa ct                                          22

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
ccgttcactg cctgaagga                                              19
```